(12) United States Patent
Berman et al.

(10) Patent No.: US 9,500,847 B2
(45) Date of Patent: Nov. 22, 2016

(54) TOTAL INTERNAL REFLECTANCE FLUORESCENCE (TIRF) MICROSCOPY ACROSS MULTIPLE WAVELENGTHS SIMULTANEOUSLY

(71) Applicant: Spectral Applied Research Inc., Richmond Hill (CA)

(72) Inventors: Richard Berman, Aurora (CA); Peter Maclean Sinclair, Toronto (CA); John Oreopoulos, Richmond Hill (CA)

(73) Assignee: Spectral Applied Research Inc., Richmond Hill (CA)

( * ) Notice: Subject to any disclaimer, the term of this patent is extended or adjusted under 35 U.S.C. 154(b) by 232 days.

(21) Appl. No.: 14/052,824

(22) Filed: Oct. 14, 2013

(65) Prior Publication Data
US 2014/0104680 A1     Apr. 17, 2014

Related U.S. Application Data

(60) Provisional application No. 61/713,232, filed on Oct. 12, 2012.

(51) Int. Cl.
*G02B 21/06* (2006.01)
*G02B 21/00* (2006.01)
(Continued)

(52) U.S. Cl.
CPC ......... *G02B 21/0076* (2013.01); *G01N 21/648* (2013.01); *G01N 21/6458* (2013.01); *G02B 21/16* (2013.01); *G02B 27/56* (2013.01)

(58) Field of Classification Search
CPC ...... G01N 21/01; G01N 21/27; G01N 21/64; G02B 21/00
USPC ....... 359/362, 363, 368, 385, 387, 388, 389, 359/390; 356/300, 301, 317, 318, 319, 320, 356/326, 328, 730, 333, 334
See application file for complete search history.

(56) References Cited

U.S. PATENT DOCUMENTS 3,999,855 A    12/1976  Hirschfeld
6,597,499 B2    7/2003  Kawano et al.
(Continued)

FOREIGN PATENT DOCUMENTS

JP    09159922     6/1997
JP    2002031762   1/2002

OTHER PUBLICATIONS

Khader, First Office Action for CA2829545, Oct. 17, 2014.
(Continued)

*Primary Examiner* — Stephone B Allen
*Assistant Examiner* — Rahman Abdur
(74) *Attorney, Agent, or Firm* — Integral Intellectual Property Inc.; Miriam Paton; Amy Scouten

(57) ABSTRACT

A multiple wavelength total internal reflection fluorescence (TIRF) microscopy system has an objective. A dispersion unit of the system comprises a high-dispersion optical element. The dispersion unit receives illumination light having at least a first wavelength $\lambda_1$ and a second wavelength $\lambda_2$, where $\lambda_1 \neq \lambda_2$, and splits the illumination light into a first monochromatic beam having the first wavelength $\lambda_1$ and a second monochromatic beam having the second wavelength $\lambda_2$. The monochromatic beams are focused onto a back focal plane of the objective, near an outer edge of the objective, at different radial distances from an optical axis of the objective. The dispersion unit is rotatable in order to adjust angles of incidence of the monochromatic beams onto an interface between a substrate and a sample to be imaged, wherein the angles of incidence are greater than the critical angle of the interface.

20 Claims, 8 Drawing Sheets

(51) Int. Cl.
  *G01N 21/64* (2006.01)
  *G02B 21/16* (2006.01)
  *G02B 27/56* (2006.01)

(56) References Cited

U.S. PATENT DOCUMENTS

| | | |
|---|---|---|
| 6,819,484 B2 | 11/2004 | Aono et al. |
| 6,924,490 B2 | 8/2005 | Natori |
| 6,987,609 B2 | 1/2006 | Tischer et al. |
| 6,992,820 B2 | 1/2006 | Abe et al. |
| 7,224,524 B2 | 5/2007 | Tsuchiya et al. |
| 7,474,462 B2 | 1/2009 | Ulrich et al. |
| 8,378,314 B2 | 2/2013 | Matthae et al. |
| 2003/0058530 A1 | 3/2003 | Kawano |
| 2012/0176672 A1* | 7/2012 | Cooper .......... G02B 21/16 359/385 |
| 2012/0176673 A1* | 7/2012 | Cooper .......... G02B 21/16 359/386 |

OTHER PUBLICATIONS

Chung, Doo Soo et al., "Fourier-transform heterodyne spectroscopy of liquid and solid surfaces", Applied Physics B 64, 1-13 (1997).
Croucher, J, Extended European Search Report for EP 13188498.3, Jan. 16, 2014.
Johnson, Daniel S. et al., "Total Internal Reflectance Fluorescence (TIRF) Microscopy Illuminator for Improved Imaging of Cell Surface Events", Current Protocols in Cytometry, 12.29.1, Jul. 2012.
Olveczky, Bence P. et al., "Mapping Fluorophore Distributions in Three Dimensions by Quantitative Multiple Angle-Total Internal Reflection Fluorescence Microscopy", Biophysical Journal, vol. 73, Nov. 1997.
Stock, K et al., "Variable-angle total internal reflection fluorescence microscopy (VA-TIRFM): realization and application of a compact illumination device", Journal of Microscopy. vol. 211, Pt 1 Jul. 2003, pp. 19-29.
Consalvo, First Exam Report for EP13188498.3 Jun. 21, 2016.

* cited by examiner

TOTAL INTERNAL REFLECTANCE FLUORESCENCE (TIRF) MICROSCOPY ACROSS MULTIPLE WAVELENGTHS SIMULTANEOUSLY

TECHNICAL FIELD

The technology relates to fluorescence microscopy and, in particular, to systems for multi-wavelength evanescent illumination of a sample in total internal reflection fluorescence (TIRF) microscopy.

BACKGROUND

Many different techniques have been developed in the field of fluorescence microscopy to restrict excitation light to a thin region of a specimen near the coverslip in order to improve the signal-to-background noise ratio and the spatial resolution of the specimen features or components of interest. Conventional widefield and laser scanning confocal fluorescence microscopy are widely employed techniques that rely on illumination of fluorophore-labeled specimens with a broad cone of light. The limited spatial resolution demonstrated by widefield fluorescence microscopy, especially along the optical axis, often renders it difficult to differentiate between individual specimen details that are overpowered by background fluorescence from outside the focal plane.

In contrast, total internal reflection fluorescence (TIRF) microscopy employs the unique properties of an induced evanescent wave to selectively illuminate and excite fluorophores in a restricted specimen region immediately adjacent to a glass-water (or glass-buffer) interface between the specimen and a transparent substrate.

The basic concept of total internal reflection fluorescence (TIRF) microscopy is simple, requiring only an excitation light beam traveling at a high incident angle through the solid glass coverslip or dish, where the cells adhere.

FIG. 1 illustrates an example of the basic concept of TIRF microscopy. Illumination light 100 is transmitted into a substrate 102, such as a coverslip, a coverplate or a slide. The illumination light 100 strikes an interface 104 between the substrate 102 and a specimen or sample 106 to be imaged at a nonzero angle of incidence 108 with respect to the interface normal. When the refractive index $n_2$ of the specimen 106 is lower than the refractive index $n_1$ of the substrate 102, that is $n_2 < n_1$, and when the angle of incidence 108 is greater than or equal to the critical angle of the interface 104, with respect to the interface normal, the light experiences total internal reflection. Thus, none of the illumination light 100 can pass into the specimen 106 and all of the illumination light 100 is reflected back into the substrate 102. However, the reflected light generates an evanescent wave with the same wavelength as the illumination light 100. The electromagnetic field of the evanescent wave penetrates beyond the interface 104 into the specimen 106 and excites fluorescence within a thin region of the specimen 106 near the interface 104. The intensity I of the evanescent field decays exponentially with increasing perpendicular distance z from the interface 104, as illustrated in FIG. 1 and as described by equation 1:

$$I(z)=I(0)e^{-z/d} \quad (1)$$

where I(z) represents the intensity at a perpendicular distance z from the interface 104, where I(0) represents the intensity at the interface 104, and where d represents the characteristic penetration depth at a wavelength λ of incident light in a vacuum. The characteristic penetration depth d is expressed by equation 2:

$$d=\lambda/(4\pi \cdot \text{sqrt}(n_1^2 \sin^2 \theta_1 - n_2^2)) \quad (2)$$

Typical penetration depths are only about 100 nanometers from the interface 104, as represented by the dashed line 112 in FIG. 1. Fluorophores of fluorescently labeled components located within the vicinity of the interface 104 can be excited by the evanescent field. A portion of the fluorescent light emitted from fluorophores near the interface 104 may be captured by an objective lens and may be used for fluorescent imaging of the specimen 106. Accordingly, this technique is useful for studying phenomena near the interface 104 between the substrate 102 and the sample 106, since other parts of the sample 106 are not illuminated at all.

FIG. 1 illustrates a schematic representation of an objective 114 used to illuminate the specimen 106 disposed on the substrate 102. The objective 114 is an oil immersion objective with immersion oil 116 disposed between the substrate 102 and a top lens 118 of the objective 114.

A common means of achieving objective-based TIRF microscopy is to focus the illumination light 100 travelling along an optical axis 115 of the microscope to a focal point near the outer edge of the objective 114 and at a back focal plane 120 of the microscope objective 114, as illustrated in FIG. 1. It should be noted that, although the back focal plane 120 is illustrated in a location that is external to the objective 114, it may alternatively be located within the objective 114. The objective 114 has a high numerical aperture (NA) in order to allow the illumination light 100 to be transmitted near the outer edges of the lenses of the objective 114 and directed into the substrate 102 with an angle of incidence 108 that supports total internal reflection. The substrate 102 and the immersion oil 116 may have nearly the same refractive index $n_1$, for example, approximately 1.52, and the specimen 106 may be in an aqueous medium with a refractive index $n_2$ of approximately 1.33 to 1.40, for example, which supports total internal reflection within the substrate 102. The NA of the objective 114 is higher than the refractive index $n_2$ of the specimen 106. The illumination light 100 strikes the substrate/specimen interface 104 with an angle of incidence 108 greater than the critical angle and is reflected back into the substrate 102 at the interface 104. The illumination light 100 creates in the specimen 106 an evanescent electromagnetic field adjacent to the interface 104.

The radial distance, for example the distance 122 in FIG. 1, of the point of light from the optical axis 115 of the objective 114 determines the angle that the light will have when leaving the objective 114. This, in turn, affects the angle of incidence 108 at the substrate/sample interface 104. Light focused further from the optical axis 115 will have a larger angle of incidence 108. By adjusting the position that the light focuses onto the objective back focal plane 120, the angle of incidence 108 can be adjusted to be near or slightly larger than the critical angle. The degree to which the angle of incidence 108 is greater than the critical angle will determine the depth of the evanescent wave and thus the imaging depth. These instruments, which use oil-immersion objectives with a high numerical aperture, are increasing in popularity today.

TIRF microscopy is an established microscopy technique with a number of implementations. FIG. 2 illustrates a possible simple TIRF implementation with a single mode fiber light delivery subsystem.

Illumination light from a single mode fiber 200 is collimated using a lens 202, and then directed via a lens 204 to a dichroic mirror 206. Illumination light incident on the dichroic mirror 206 is focused onto a back aperture 208 of an objective 210 at a desired radial distance R 212 from the optical axis 213 of the objective 210. The radial distance R 212 is adjustable by laterally moving optical elements such as the single mode fiber 200 or the lens 202 or the lens 204, where the lateral direction is denoted by an arrow 224 in FIG. 2.

The objective 210 directs the illumination light, via a hemispherical lens 222, through a substrate 214 and into a sample 216 to be imaged. The illumination light may strike the interface between the substrate 214 and the sample 216 with angles of incidence that are greater than the critical angle, such that total internal reflection is achieved.

Fluorescent light emitted from the sample 216 near the substrate/sample interface may be captured by the hemispherical lens 222 of the microscope objective 210 at the operating numerical aperture NA of the microscope objective 210. The collected fluorescent light further passes through the dichroic mirror 206 and is focused by a tube lens 218 onto an image plane which coincides with an image sensor of an imaging device 220.

Varying an incidence angle of the illumination light or a depth along which observation should be carried out is usually accomplished in the objective-based TIRF microscopy instrument by varying the radial distance of the focused light spot of the illumination light at the back focal plane of the microscope objective. The lateral displacement can be implemented through any of a plurality of technically simple means. For example, in such a microscope, a pick-off member, which reflects the light from a light source to a sample, may be placed in the back focal plane. The pick-off member may be in the form of a small mirror, as described in JP9159922A. Alternatively, the pick-off member may be in the form of a right angle prism, as described in U.S. Pat. No. 6,987,609. A displacement of the pick-off member in the radial direction away from the optical axis of the objective leads directly to a corresponding change in the angle of incidence of the illumination light and the penetration depth of the TIRF imaging.

In another example, radial beam displacement may be achieved using deflection means such as a steering mirror (as described in JP2002031762) or an acousto-optical modulator (as described in US Patent Application Publication No. 20030058530), in combination with a focusing lens. The radial beam adjustment may be done by a lateral movement of the tip of a light delivering optical fiber, as described in U.S. Pat. No. 6,924,490, or by lateral movement of a focusing lens, as described in U.S. Pat. No. 6,992,820. The TIRF microscope described in U.S. Pat. No. 7,224,524 comprises an optical device in the form of a wedge plate which is disposed on the optical path of the optical illumination system and de-centers an optical axis of the light beam.

SUMMARY

Objective-based TIRF microscopes present several challenges when dealing with multiple wavelength TIRF. For example, multiple wavelength TIRF microscopes use a multiple wavelength illumination beam directed along the outer edge of the lenses of the objective. However, because the critical angle is invariably wavelength dependent, differing wavelengths will have different angles of incidence. This can mean that some wavelengths of light will be totally internally reflected, while others will not be totally internally reflected. It can also mean that different wavelengths will image to differing depths within the sample.

A typical light source for TIRF microscopy is laser light transmitted through a single mode fiber, as described, for example, in U.S. Pat. No. 6,819,484, U.S. Pat. No. 6,987,609, and U.S. Pat. No. 6,992,820). However, broadband radiation light sources have been used with narrow annular diaphragms, as described in U.S. Pat. No. 6,597,499 and U.S. Pat. No. 7,474,462, or with crescent-shaped slits, as described in U.S. Pat. No. 7,224,524, where the annular diaphragms or slits limit the spatial extent of the light in the radial dimension.

Several solutions have been used to enable imaging across multiple wavelengths. The most basic solution is to adjust the position of the incoming light source such that the radial distance of the focused light spot at the back focal plane of the objective can be adjusted laterally. The adjustment can be done manually or with an automated actuator. In either case, simultaneously imaging at multiple wavelengths is compromised, as a single light source can only be focused at one location at a time. Often this means sequentially changing the focus position with wavelength changes. However, there are disadvantages to switching between the different excitation wavelengths by mechanically steering and refocusing the multiple wavelength beam so that a selected wavelength strikes the interface with an angle of incidence greater than the critical angle for each wavelength. This process takes time, it prevents simultaneous imaging with more than one wavelength, and it requires additional mechanical systems to change the position of a focal point of the illumination beam in the objective back focal plane, which increases the cost of an objective-based TIRF microscope.

To overcome this shortcoming, Olympus Corporation headquartered in Tokyo, Japan has introduced a system called the cell^TIRF® that uses four fibers that can be independently positioned. This allows four different wavelengths to be used simultaneously. However, it complicates the instrument, the alignment, and the originating light source, which is often a multitude of lasers.

U.S. Pat. No. 8,378,314 describes an apparatus that comprises correction optics providing a transverse chromatic aberration which is pre-configured in such a way that the wavelength-dependent differences of the penetration depth in the evanescent illumination of the sample are partially corrected. The chromatic aberration component is built in the form of a multi-component lens or an oblique planar plate. U.S. Pat. No. 8,378,314 discloses that the system should be designed to achieve a predetermined chromatic aberration to account for an assumed system having a particular microscope objective, particular indices of refraction of the oil, the coverslip, and sample, and particular illumination wavelengths. A well-known problem with this implementation is that it is rare for all of these factors to be known a priori. Accordingly, the system proposed in U.S. Pat. No. 8,378,314 may not be particularly useful in actual applications where numerous wavelengths are used and sample media change from sample to sample.

To address the problems with the state of the art, an adjustment device may be designed to distribute the focal spots of multiple light beams of different wavelengths provided by a single mode fiber to different radial locations on the back focal plane of the oil immersion microscope objective, thus providing desired angles of incidence of the light onto a substrate/sample interface and desired depths of the evanescent waves of different wavelengths. For these purposes, the adjustment device may comprise a dispersive unit providing controlled chromatic dispersion of the multi-wavelength illuminating light and splitting the multi-wavelength illuminating light into a set of monochromatic beams required, for example, to achieve the same illumination depths for the different wavelengths used. The adjustment device may also comprise a beam steering means providing a desired simultaneous shift of a whole set of the individual focal points of different wavelengths without varying the radial distances between them.

The technology described herein relates to a method and a device for the evanescent illumination of a sample for TIRF microscopy, in which the wavelength-related differences of the penetration depths can be reduced in a manner that is tunable to the imaging conditions presented.

In one example, there is provided an adjustable dispersive device for the evanescent illumination of a sample that provides controlled chromatic dispersion—the relative separation of at least two focal spots in the back focal plane of the objective—of the illuminating light using a single dispersive optical flat with a tunable angle of incidence. Changing the angle of incidence by rotating the optical flat will change the dispersive effect of the optical flat. Larger angles of incidence will correspond to greater lateral separation of optical beams with differing wavelengths. In this manner, the difference in radial positions as a function of wavelength can be tuned. This tuning can, to some degree, correct for differences in the critical angle as a function of wavelengths.

As the optical flat is rotated, not only is the dispersive effect tuned but the absolute offset of the optical beam is also varied. In addition, the total path length through the optical flat is changed, which in turn changes the axial focal position of the focused spots near the back focal plane of the objective. Although, both of these effects can be corrected by using other alignment optics, in practice it is inconvenient and difficult to account for the full range of adjustment in both lateral and axial dimensions.

In another example, the shift in axial focus is reduced along with other optical aberrations. The adjustment device comprises a dispersive unit in the form of two optical flats oriented in a V formation, one flat of a highly dispersive glass and one of a low dispersion glass. Such a dispersive unit for the evanescent illumination of a sample that provides controlled chromatic dispersion—relative distance between at least two focal spots in the back focal plane of the objective—but results in less axial chromatic aberration and hence less axial focus shift. This formation also creates fewer optical aberrations, such as astigmatism or spherical aberration. In this manner, the corrections required to account for the focus displacement may be unnecessary.

Additional adjustment of the absolute radial locations of the focal spots of the multi-wavelength excitation light beams on the back focal plane of the microscope objective may be required, for example, when the TIRF microscope is used for imaging a sample at different penetration depths, or, alternatively, a number of samples under investigation having different refractive indexes.

The technology described herein may enable multiple wavelengths to be used simultaneously with closely matched image TIRF penetration depths.

R is used herein to denote an absolute radial distance of a focal point from an optical axis of an objective at (or near) the back focal plane of the objective.

$R(\lambda_1)$ may be used to denote the distance R for a focal point of a monochromatic beam of a first wavelength $\lambda_1$. $R(\lambda_2)$ may be used to denote the distance R for a focal point of a monochromatic beam of a second wavelength $\lambda_2$. Some implementations of the dispersion unit may provide positive dispersion of the multi-wavelength excitation light when $R(\lambda_1)>R(\lambda_2)$, $\lambda_1>\lambda_2$, and negative dispersion when $R(\lambda_1)<R(\lambda_2)$, $\lambda_1>\lambda_2$. The dispersion unit may be used for obtaining closely matched image TIRF penetration depths for a whole range of desired penetration depths, for example, from approximately 100 nm to 200-300 nm. The dispersion unit may also be used for a plurality of objective-sample combinations.

Some implementations of the controllable dispersive unit for the evanescent illumination of a sample may show low undesired optical aberrations.

Rotation of the dispersion unit may allow the user to tune the relative penetration depths for illumination light of different wavelengths in order to achieve depths that are as similar as possible. This may be done without knowledge of the optical properties of microscope, objective, sample or substrate. By using a sample with defined structure, such as small beads, the angle of the dispersion unit may be tuned to closely match the imaging depth across a number of wavelengths.

The terms "light" and "radiation" may be used interchangeably and refer to light in the UV-visible-NIR (ultraviolet-visible-near infrared) spectral range. The terms "light source" and "radiation source" may refer to any source able to generate and emit light or radiation, including but not limited to, lasers, light emitting diodes (LEDs), solid state devices, super luminescent diodes (SLDs), arc lamps, or any other suitable light sources as would be apparent to someone skilled in the art.

"Illumination light" or "excitation light", as used herein, refers to any light provided by a light source to be used for evanescent illumination of a sample. "Emission light" or "returned light" refers to the light returning from the sample, and used for obtaining images of the sample. The returned light is often produced by fluorescence of a sample illuminated with the excitation light.

A "reference wavelength", as used herein, refers to one of wavelengths of the multiple wavelength illumination light. For the sake of definiteness, the shortest wavelength may be taken as the reference wavelength.

The term "evanescent illumination" or "total internal illumination", as used herein, refers to the illumination light which is incident on the interface between a substrate and a sample at an angle of incidence that is greater than or equal to the critical angle of reflection. At these angles, all light is reflected but the electromagnetic field of the evanescent wave produced by the illumination light is available at small depths in the sample, thus providing excitation of fluorescence within a thin region of the sample near the interface.

An "optical path length (OPL)" or "optical distance", as used herein, refers to a sum of the products of the geometric lengths of the paths that light follows through optical components and/or media, and the respective indices of refraction of those optical components and/or media. A difference between two optical path lengths is called an optical path difference (OPD).

As used herein, a "microscope" comprises at least a microscope objective lens, as illustrated, for example, by the objective 114 in FIG. 1, and by the objective lens 210 in FIG. 2. In other examples, microscopes may be considered to have the more conventional form of an infinity corrected micro-objective and a tube lens. Both cases are interchangeable. A "microscope system" is a system that may be used to probe a sample by providing an evanescent illumination of the sample, thus producing fluorescence light from the sample.

BRIEF DESCRIPTION OF THE DRAWINGS

FIGS. 4-1 and 4-2 illustrate magnified views of the dispersion unit of the objective-based TIRF microscopy system of FIG. 3.

FIGS. 7-1, 7-2, and 7-3 illustrate magnified views of the dispersion unit of the objective-based TIRF microscopy system of FIG. 6.

It will be appreciated that for the simplicity and clarity of illustration, elements shown in the figures have not necessarily been drawn to scale. For example, the dimensions of some of the elements may be exaggerated relative to other elements for clarity purposes.

DETAILED DESCRIPTION

Figure 3:
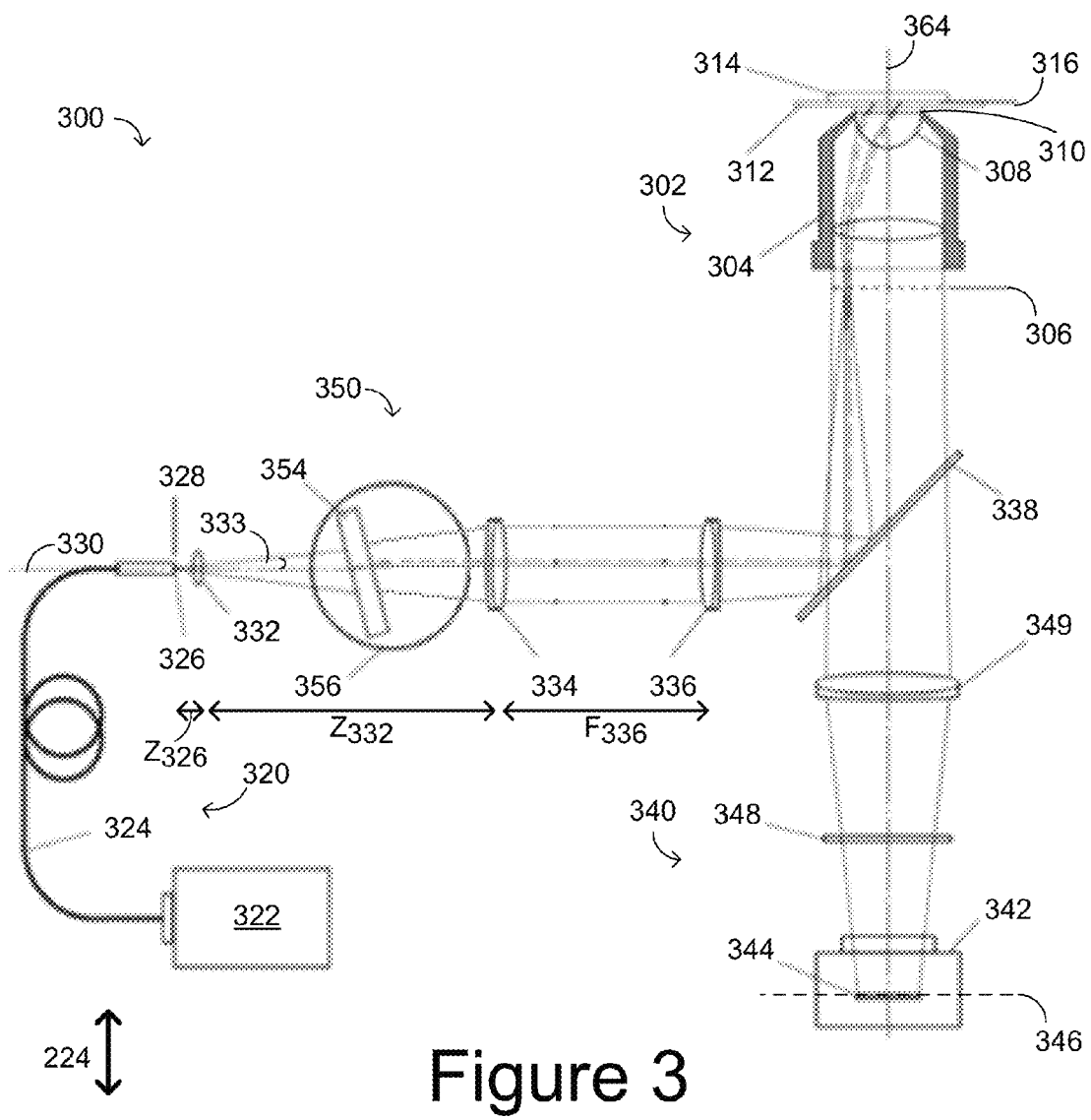
FIG. 3 illustrates a schematic view of an example TIRF microscopy system for multi-wavelength evanescent illumination of a sample.

FIG. 3 illustrates a schematic representation of an example objective-based multiple wavelength TIRF microscopy system 300.

The system 300 includes a microscope 302 comprising a high numerical aperture oil immersion objective 304 with a back focal plane 306 and a hemispherical top lens 308. It should be noted that although the back focal plane 306 is illustrated in a location that is external to the objective 304, the back focal plane 306 may alternatively be located within the objective 304. The lens 308 is placed into contact with immersion oil 310, which in turn is placed into contact with a substrate 312, such as a coverslip. The substrate 312 contacts a sample 314 at a substrate/sample interface 316.

The system 300 includes an illumination module 320 configured to provide a beam of illumination light of at least two different wavelengths. The illumination module 320 comprises a light source 322. In one example, the light source 322 is in the form of the multi-wavelength radiation source assembly described in U.S. Pat. No. 8,275,226, which is configured to generate and optionally to condition multi-wavelength radiation that is suitable for illumination in TIRF microscopy. Depending on the application, the light source 322 may comprise two or more lasers, each laser generating light at a different wavelength, for example.

For the sake of simplicity and brevity in the following description, the illumination light is composed of a mixture of at least two wavelengths: a first wavelength $\lambda_1$ (also known as the reference wavelength) and a second wavelength $\lambda_2$, where the wavelength $\lambda_1$ is shorter than the wavelength $\lambda_2$.

The light source 322 may be coupled to a fiber optic light delivery subsystem, which may include one or more lenses (not shown), one or more mirrors (not shown), and/or one or more prisms (not shown). The fiber optic light delivery subsystem is illustrated in FIG. 3 in the form of a single mode optical fiber 324. A distal end tip 326 of the optical fiber 324 may be mounted in a plane 328 that is conjugate to the back focal plane 306 of the objective 304.

The optical fiber 324 has a numerical aperture $NA_F$, which is related to the half-angle $\theta_F$ 333 illustrated in FIG. 3. In general, a numerical aperture $NA_F$ of a fiber is expressed by equation 3 as:

$$NA_F = n \sin \theta_F \qquad (3)$$

where n is a refractive index of the surrounding medium to which the light exits from the distal end 326 of the fiber 324, and the exit angle $\theta_F$ is the angle of divergence of light with respect to an optical axis 330 of the fiber 324. In the case that the surrounding medium is air, the refractive index n=1. Common values for the numerical aperture $NA_F$ of a single mode fiber range from 0.10 to 0.15, and, for visual light, $NA_F \approx 0.12$-0.13.

In order to collimate the light beam emerging from the fiber tip 326, a collimating lens 334 having a focal length $F_{334}$ may be placed at an optical distance $F_{334}$ from the fiber tip 326.

An imaging lens 336 having a focal length $F_{336}$ may be used to focus the previously collimated beam emerging from the collimating lens 334 onto the back focal plane 306 of the objective 304, via a dichroic mirror 338. The light may also be reflected off of an optional folding mirror (not shown). For superior system performance, the imaging lens 336 may be placed at an optical distance $F_{336}$ from the collimating lens 334. The lenses 334 and 336 form a relay optical device providing an image of the fiber tip 326 onto the back focal plane 306.

The system 300 includes an imaging module 340 which comprises an imaging device 342, such as a high-sensitivity camera, and an optional blocking filter 348. The imaging device 342 comprises an image sensor 344, and may be positioned such that a front face of the image sensor 344 coincides with an image plane 346 that is conjugate to a sample plane adjacent to the substrate/sample interface 316.

A non-exhaustive list of examples of the imaging device 342 includes a charge-coupled device (CCD) camera, a complementary metal-oxide semiconductor (CMOS) camera, an intensified CCD (ICCD) camera, and any other suitable camera as would be apparent to someone skilled in the art. A 3CCD camera with additional narrowband filters may be applied for simultaneous multi-spectral imaging. Alternatively, the emission light may be split using dichroic mirrors to simultaneously image different wavelength bands on separate imaging devices.

Fluorescent light emitted from the sample 314 near the interface 316 may be captured by the hemispherical lens 308 of the microscope objective 304 at the operating numerical aperture of the microscope objective 304. The collected fluorescent light further passes through the dichroic mirror 338 and the optional blocking filter 348, and is focused by a lens 349 onto the image plane 346 coinciding with a detection plane of the image sensor 334 of the imaging device 342, where it may be captured.

The system 300 includes a dispersion unit 350 which will be described in more detail below.

To improve operation of the system 300 and to decrease spherical aberration and astigmatism induced by the dispersion unit 350, it may be of interest to lower the numerical aperture of the illumination beam exiting the fiber tip 326. This may be achieved by placing optional light divergence control optics 332 at a predetermined distance from the fiber tip 326.

In one example, a desired beam aperture may be obtained by placing, at a distance $Z_{326}$ from the fiber tip 326, light divergence control optics 332 in the form of an achromatic lens having a focal length $F_{332}$ and a numerical aperture $NA_{332}$. The distance $Z_{326}$ from the fiber tip 326 may be found by using the thin lens approximation and paraxial approximation, and is expressed in equation 4 as:

$$Z_{326}=F_{332}(1-NA_F/NA_{332}) \quad (4)$$

The collimating lens 334 may be placed at a predetermined optical distance $Z_{332}$ from the lens 332, where the distance $Z_{332}$ may be found by using the thin lens approximation and paraxial approximation, and is expressed in equation 5 as:

$$Z_{332}=F_{334}=F_{332}(NA_{332}/NA_F-1) \quad (5)$$

While the divergence control optics 332, the collimating optics 334, and the imaging optics 336 are presented in the form of achromatic doublet lenses, they may alternatively be built in the form of aspherized achromatic, gradient index, triplet, or multi-component lenses, or any other focusing elements, including reflective focusing elements, as would be apparent to someone skilled in the art.

The dispersion unit 350 may be designed to distribute the focal spots of at least two light beams of at least two different wavelengths originating from the fiber tip 326 to at least two different radial locations on the back focal plane 306 of the high numerical aperture objective 304, thereby providing desired angles of incidence of the light onto a substrate/sample interface 316 and desired depths of the evanescent waves of illumination light of the at least two different wavelengths. The dispersion unit 350 provides controlled chromatic dispersion of the illuminating light of at least two different wavelengths and splitting the at least two-wavelength light into at least two monochromatic beams required, for example, to achieve the same illumination depths for the different wavelengths used. The dispersion unit 350 may also comprise a beam shifting means (not shown) providing a desired simultaneous absolute offset of a whole set of the at least two individual focal points of different wavelengths without varying the radial distances between them.

The dispersion unit 350 may be configured to provide controlled chromatic dispersion of illuminating light of at least two different wavelengths. The dispersion unit 350 may be implemented in the form of a single optical flat 354 which may be mounted on a rotatable plate 356. The rotatable plate 356 is rotatable about an axis perpendicular to the plane of the rotatable plate 356.

Figure 1:
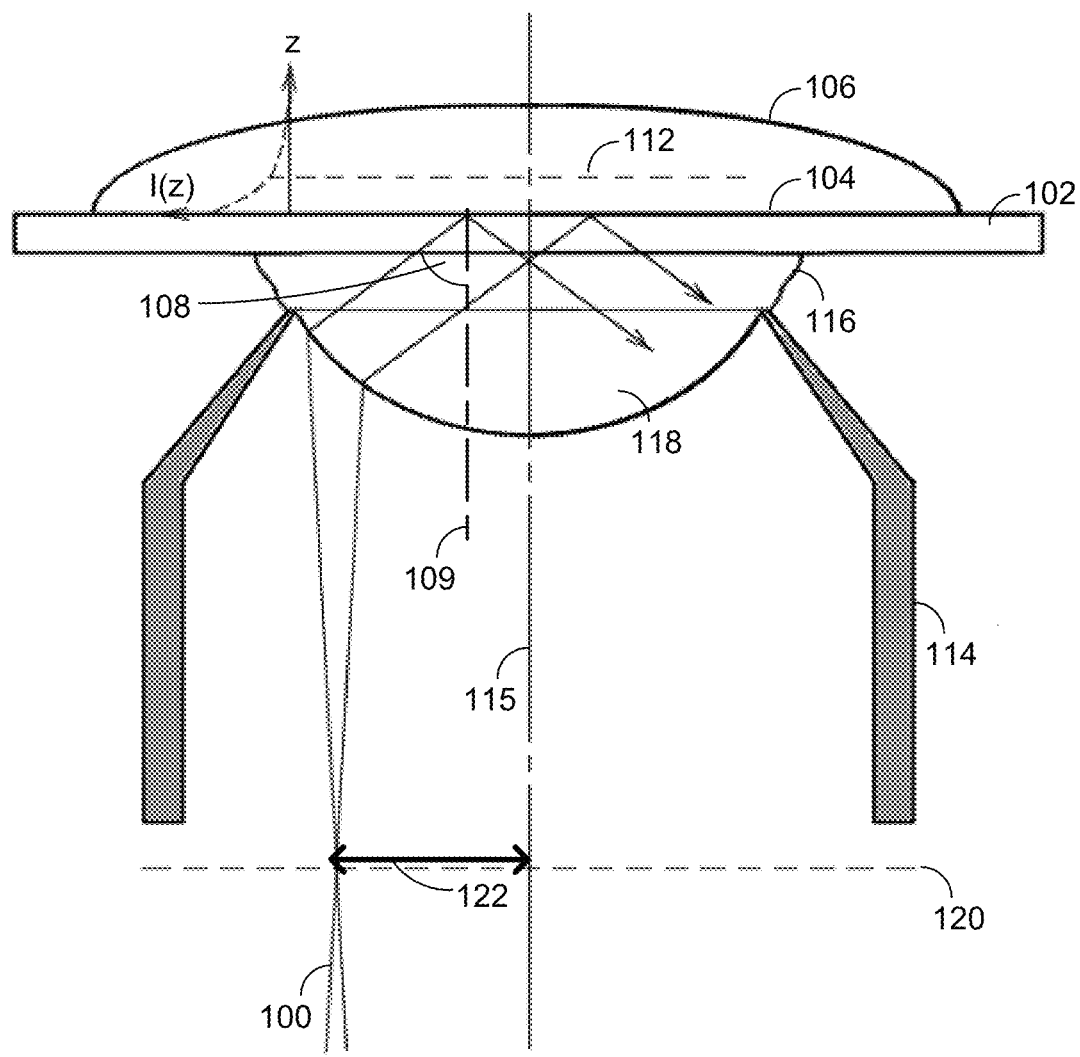
FIG. 1 illustrates the operational principle of objective based TIRF microscopy according to prior art.
Figure 2:
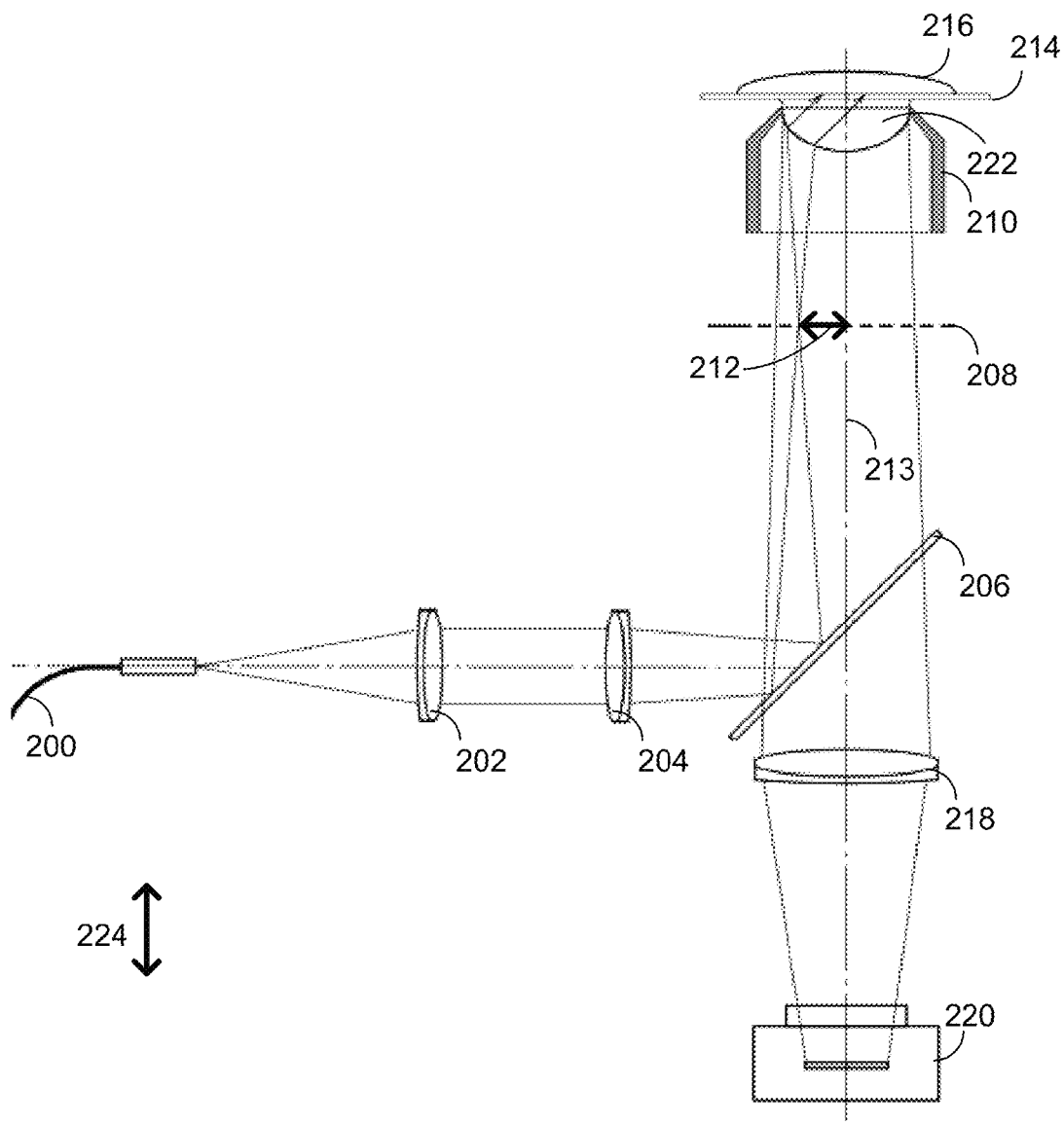
FIG. 2 illustrates a schematic view of a single wavelength objective based TIRF microscope according to prior art.
Figures 1, 4:
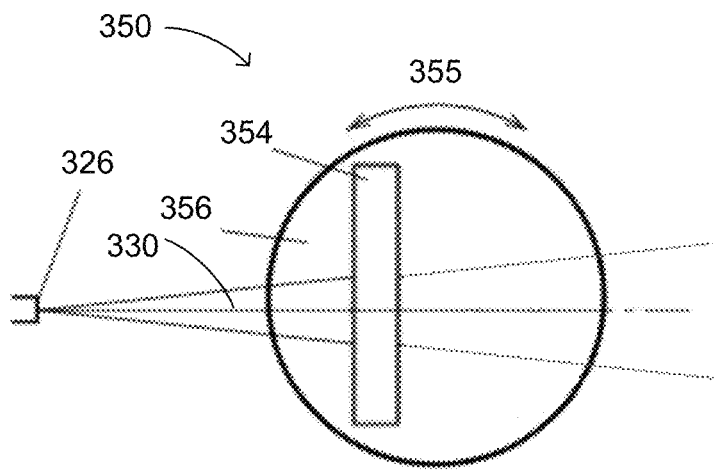
Figures 2, 4:
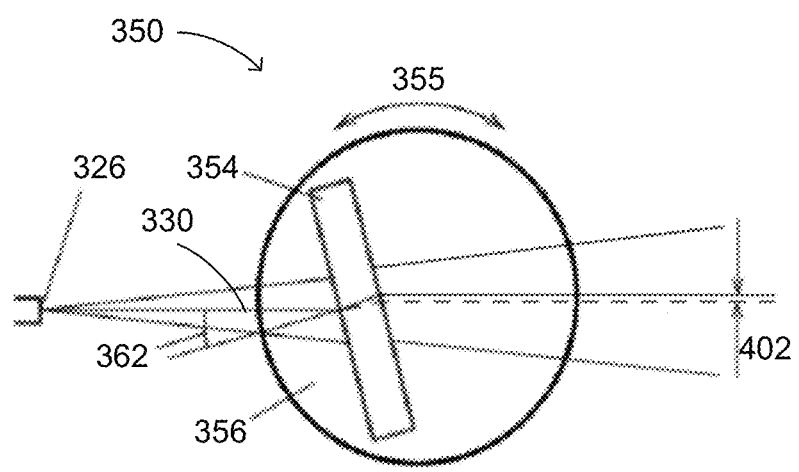

FIGS. 4-1 and 4-2 illustrate the example dispersion unit 350 in different orientations.

$\alpha$ 362 represents an angle of the normal of the optical flat 354 relative to the optical axis 330. The direction of rotation of the rotatable plate 356 is denoted by the arrow 355.

In FIG. 4-1, the dispersion unit 350 is in its central position such that the angle $\alpha$ 362 is zero. In FIG. 4-2, the dispersion unit 350 is oriented such that the angle $\alpha$ 362 is greater than zero.

The optical flat 354 is a highly dispersive optical element. In one example, the optical flat 354 may be made of optical glass SF11 or of optical glass SF10. The dispersion of the optical flat 354 leads to a distance between chief rays $s_{354}(n,\alpha)$ of at least two beams with different wavelengths $\lambda_1$ and $\lambda_2$, expressed by equation 6 as:

$$s_{354}(t_{354},n_{354},\alpha)=t_{354}\sin\alpha(\cos\alpha\cdot\Delta n_{354}/(n_{354}^2-\sin^2\alpha)^{3/2}) \quad (6)$$

where $t_{354}$ is the thickness of the optical flat 354, and $n_{354}$ is an average index of refraction which may be found using equation 7:

$$n_{354}=[n_{354}(\lambda_1)+n_{354}(\lambda_2)]/2=N_{354}-\Delta n_{354}/2 \quad (7)$$

where $\Delta n_{354}=n_{354}(\lambda_1)-n_{354}(\lambda_2)$, and where $N_{354}=n_{354}(\lambda_1)$.

In general, $N_K=n_K(\lambda_1)$ may be used herein to represent the refractive index of the optical flat K at the reference wavelength $\lambda_1$, where $\lambda_1<\lambda_2$.

The absolute offset $y_{354}$ provided by the optical flat 354 is expressed by equation 8 for the reference wavelength $\lambda_1$ as:

$$y_{354}(t_{354},n_{354},\alpha)=t_{354}\sin\alpha(1-\cos\alpha/\sqrt{n_{354}^2-\sin^2\alpha}) \quad (8)$$

The absolute offset $y_{354}$ is denoted by 402 in FIG. 4-2.

By rotating the single-plate dispersion unit 350, a range of offsets may be provided for the at least two beams of different wavelengths.

Adjustment of the absolute offset and compensation of the undesired absolute offset may be achieved by simultaneous radial shift of the at least two individual focal points of different wavelengths provided by means of lateral movement of the distal tip 326 of the single mode fiber 324, where the lateral direction is denoted by arrow 224.

Alternatively, compensation of the absolute lateral offset may be achieved by means of lateral movement of the collimating lens 334.

In another example, compensation of the absolute lateral offset may be achieved by means of lateral movement of the imaging lens 336.

In another example, compensation of the absolute lateral offset may be achieved by means of movement of the dichroic mirror 338 along an optical axis 364 of the microscope module 302 or along the optical axis 330 or along both.

In another example, compensation of the absolute lateral offset may be achieved by using any other suitable beam shifting means providing a desired simultaneous radial shift of the at least two individual focal points, as would be apparent to someone skilled in the art. The beam shifting means may be part of the dispersion unit 350.

In yet another example, compensation of the absolute lateral offset may be achieved by means of steering an optional folding and steering mirror (not shown) or any other beam steering means placed between the collimating lens 334 and the imaging lens 336, as would be apparent to someone skilled in the art.

In practice, a single lens or more than the two lenses 334 and 336 and additional mirrors may be used to direct and control the path of light output from the tip 326 of the fiber 324 and to input the light to the objective 304.

IN OPERATION: Illumination light of at least two different wavelengths, $\lambda_1$ and $\lambda_2$, is delivered from the light source 322 through the single mode optical fiber 324. The light diverges or spreads out from the distal end 326 of the fiber 324, and passes through the optional divergence control lens 332 and through the optical flat 354 of the dispersion unit 350.

The illumination light is split by the optical flat 354 into at least two beams of different wavelengths, $\lambda_1$ and $\lambda_2$, with a distance between chief rays $s_{354}(t_{354}, n_{354}, \alpha)$ given by equation 6, and an offset $y_{354}$ given by equation 8. The absolute offset of the at least two beams of different wavelengths may be compensated, for example, by means of lateral movement of the distal tip 326 of the fiber 324. After passing through the dispersion unit 350, the chief rays parallel to the optical axis 330 pass through the collimating lens 334. The light is collimated by the collimating lens 334, which provides at least two collateral partially overlapping collimated beams travelling toward the imaging lens 336. The light is refocused by the imaging lens 336 before being reflected by the dichroic mirror 338 along the optical axis 364 and toward the outer edge of the back focal plane of the microscope objective 304.

The imaging lens 336 focuses the illumination beams onto (or close to) the back focal plane 306 of the objective 304, so that the lenses 334 and 336 provide an image of the fiber tip 326 onto the back focal plane 306.

Figure 5:
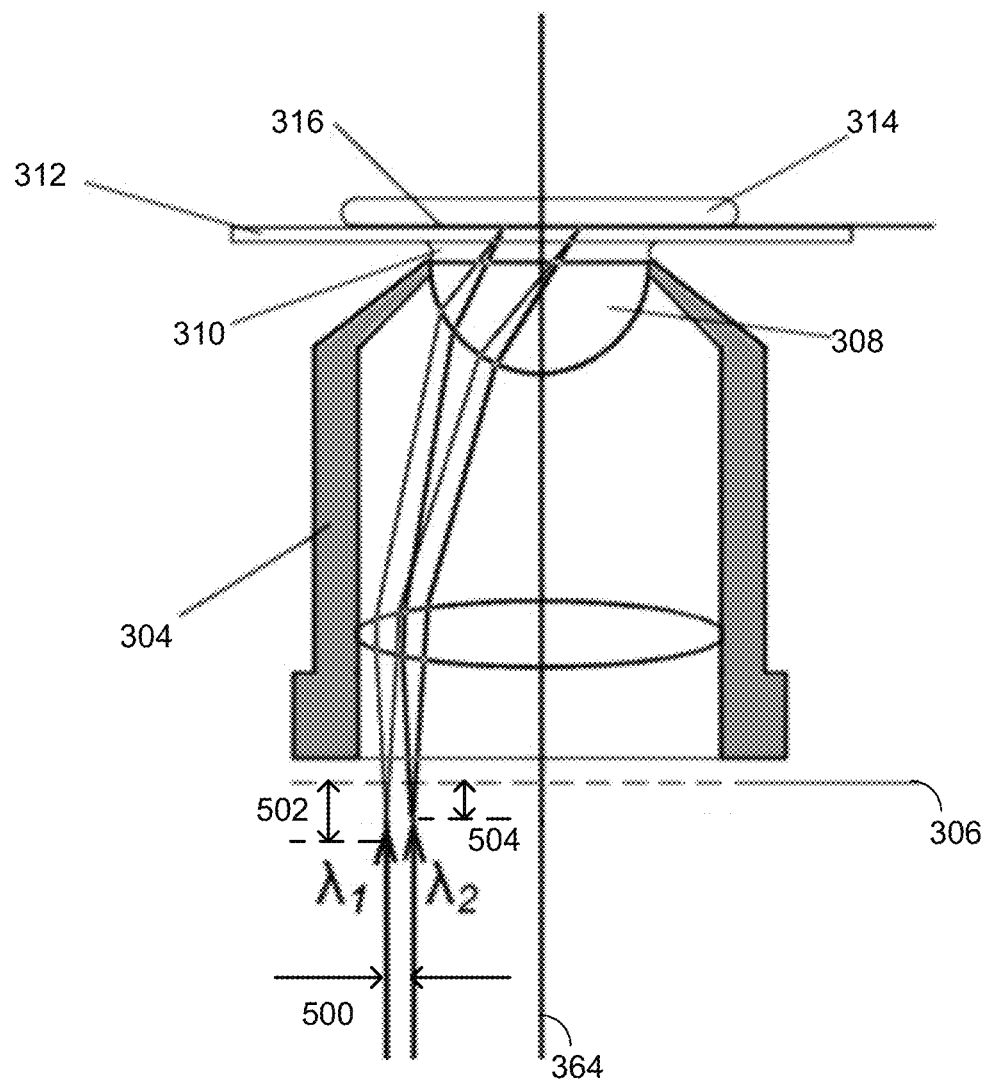
FIG. 5 illustrates a magnified view of the objective lens with the sample in the objective-based TIRF microscopy system of FIG. 3.

The relative distance ΔR between the two focal points of the different wavelengths, $\lambda_1$ and $\lambda_2$, is illustrated at 500 in FIG. 5 and is expressed by equation 9 as:

$$\Delta R = y_{354} \cdot F_{336}/F_{334} \qquad (9)$$

The objective 304 directs the beams of illumination light travelling along the outer edge of the objective lenses of the objective 304 so that light exiting the hemispherical lens 308 and passed through the immersion oil 310 and the substrate 312 strikes the interface 316 between the sample 314 and the substrate 312 with angles of incidence that are greater than the critical angle and provide the desired depths of the evanescent waves of illumination light of the at least two different wavelengths.

The objective 304 has a high numerical aperture NA in order to allow the at least two beams of illumination light of different wavelengths $\lambda_1$ and $\lambda_2$, focused separately onto (or close to) the back focal plane 306, to be transmitted near the outer edge of the microscope objective 304 and directed into the substrate 312 with an angle of incidence that supports total internal reflection. The at least two-wavelength light may be present simultaneously or one at a time or in any combination of wavelengths simultaneously. For aqueous mounts, the refractive index $n_2$ of the sample 314 may be greater than 1.33, that is $n_2 > 1.33$. In one example, the substrate 312 and the oil 310 have nearly the same refractive index $n_1$ of approximately 1.52, and the sample 314 is in an aqueous medium with a refractive index $n_2$ of approximately 1.33-1.40. This supports total internal reflection on the substrate/sample interface 316. The numerical aperture NA of the microscope objective 304 is higher than the refractive index $n_2$ of the sample.

Rotation of the dispersion unit 350 and lateral shifting of the fiber tip 326 may allow the user to adjust the radial locations R of the focal spots of at least two converging monochromatic light beams of two different wavelengths on (or near) the back focal plane 306. As a result, it is possible to tune the relative penetration depths of evanescent illumination light of different wavelengths, for example, to obtain depths that are as similar as possible for different wavelengths.

Additional adjustment of the radial locations R of the focal spots of the at least two different wavelengths on (or near) the back focal plane 306 may be of interest, for example, when seeking to image a sample at different penetration depths, or, alternatively, when imaging a number of different samples having different refractive indexes.

Fluorescent light emitted from the sample 314 near the interface 316 may be captured by the hemispherical lens 308 of the microscope objective 304 at the operating numerical aperture NA of the microscope objective 304. The collected fluorescent light further passes through the dichroic mirror 338 and the blocking filter 348, and is focused by the lens 349 onto the image plane 346, which coincides with a detection plane of the image sensor 344 of the imaging device 342. The collected fluorescent light may alternatively be separated into different wavelength ranges and simultaneously imaged on multiple imaging devices as would be apparent to one skilled in the art.

When the optical flat 354 is set to an angle other than normal incidence to the optical axis 330, as illustrated in FIG. 4-2 for example, aberrations, such as astigmatism, may occur at the back focal plane 306 of the objective 304.

In addition, the presence of the optical flat 354 when angled relative to the illumination beam may cause the focal points to shift away from the back focal plane 306 along the axis 364. This is described in more detail with respect to FIG. 5.

FIG. 5 illustrates a magnified view of the objective 304 with the sample 314 in the objective-based TIRF microscope system 300 of FIG. 3.

As described previously, the system 300 provides illumination of the sample 314, which is disposed on the substrate 312. The objective 304 is an oil immersion objective with immersion oil 310 disposed between the substrate 312 and the hemispherical lens 308 of the objective 304.

The presence of the optical flat 354 may cause the locations of the focal points of the illumination beams having wavelengths $\lambda_1$ and $\lambda_2$ to shift in a direction parallel to the optical axis 364. This is illustrated schematically in FIG. 5 by the distances 502 and 504, which represent the respective axial shifts of the monochromatic beams for wavelengths $\lambda_1$ and $\lambda_2$ relative to the back focal plane 306.

To address the aberrations and/or axial shifting of the focal spots relative to the back focal plane, a second optical flat may be added to the dispersion unit. The second optical flat has a lower index of refraction than the first optical flat.

The second optical flat may be inserted into the optical beam path at an angle relative to the first optical flat. In one example, a normal of the first optical flat and a normal of the second optical flat have an angle of 30° between them. The two optical flats may be fixed or mounted to a rotatable plate or platform such that, as the first optical flat rotates about an axis by some angular amount, the second optical flat rotates about the axis by the same angular amount.

The second optical flat may be angled with respect to the first optical flat to reduce any aberrations, such as astigmatism, that occur at the back focal plane of the objective lens.

A thickness of the second optical flat may be selected such that the optical path length of the illumination beams is almost the same regardless of what angle the pair of optical flats is rotated by, thereby minimizing the amount of axial focus change at the back-focal plane of the objective. In one example, the pair of optical flats may be rotated between a minimum of 0° and a maximum of 30°.

With the thickness and the index of refraction of the first optical flat fixed, and the refractive index of the second optical flat fixed, the thickness of the second optical flat may be selected by solving a mathematical expression that matches the optical path lengths for the two angular extremes, such as 0° and 30°. For intermediate angular positions, the optical path length may be nearly maintained with this thickness.

The precise axial spacing between the two optical flats should be small enough to ensure that the illumination beams pass fully through both faces of the optical flats at all angular positions without clipping on the optical flat edges. This also applies for the lateral size and dimensions of the optical flats.

Figure 6:
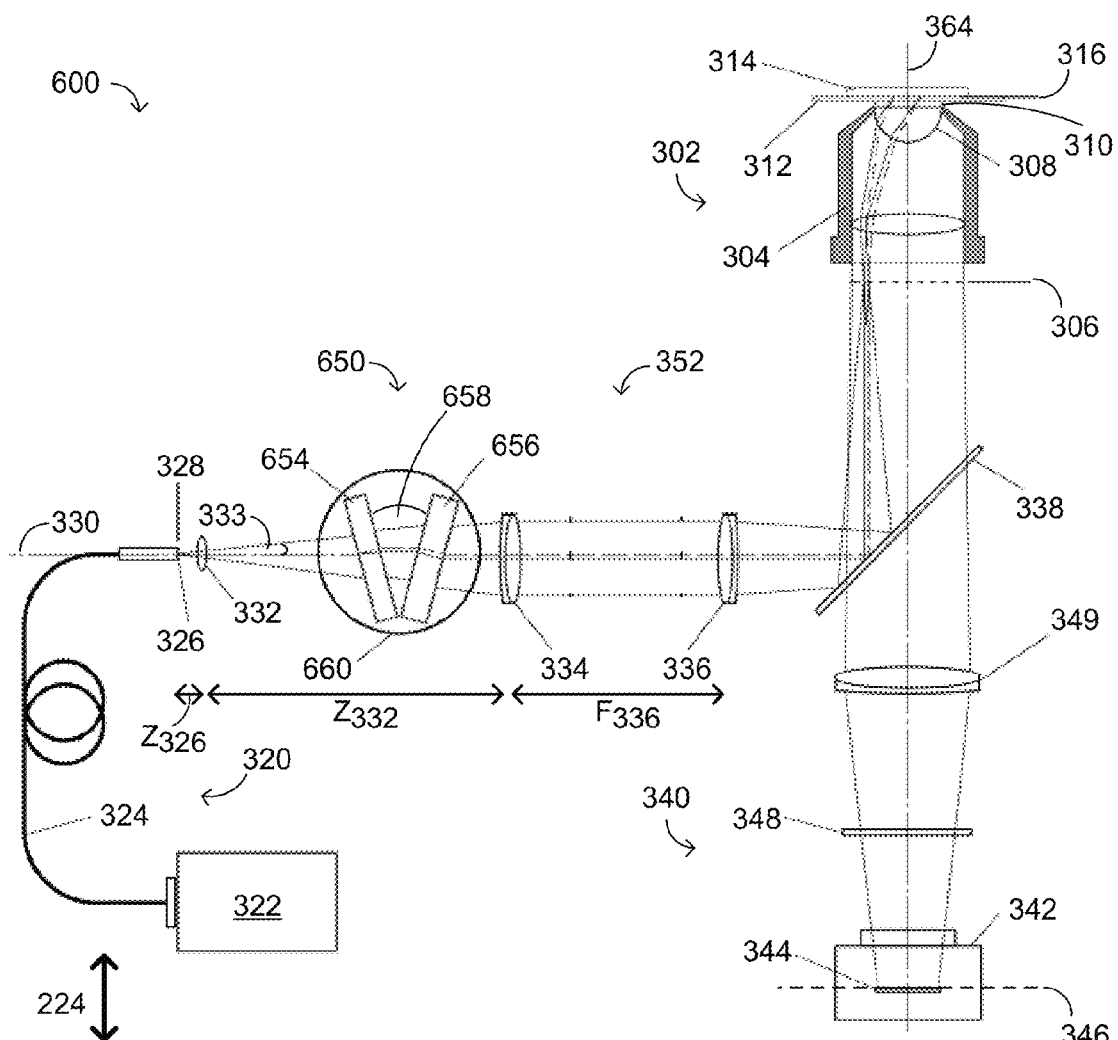
FIG. 6 illustrates a schematic view of another example TIRF microscopy system for multi-wavelength evanescent illumination of a sample.

FIG. 6 illustrates a schematic representation of an example objective-based multiple wavelength TIRF microscopy system 600.

The example TIRF microscopy system 600 includes a dispersion unit 650.

As described previously with respect to FIG. 3, illumination light of at least two different wavelengths, $\lambda_1$ and $\lambda_2$, is delivered from the light source 322 through the single mode optical fiber 324. The light diverges or spreads out from the distal end 326 of the fiber 324, and passes through the optional divergence control lens 332.

The light from the imaging lens 336 is incident on the dispersion unit 650.

The light exiting the dispersion unit 650 is collimated by the collimating lens 334, and then refocused by the imaging lens 336.

The light is then reflected by the dichroic mirror 338 along the optical axis 364 and toward the outer edge of the back focal plane of the microscope objective 304. The imaging lens 336 focuses the illumination beams onto the back focal plane 306 of the objective 304, so that the lenses 334 and 336 provide an image of the fiber tip 326 onto the back focal plane 306.

As described previously with respect to FIG. 3, fluorescent light emitted from the sample 314 near the interface 316 may be captured by the hemispherical lens 308 of the microscope objective 304 at the operating numerical aperture NA of the microscope objective 304. The collected fluorescent light further passes through the dichroic mirror 338 and the blocking filter 348, and is focused by the lens 349 onto the image plane 346, which coincides with a detection plane of the image sensor 344 of the imaging device 342. The collected fluorescent light may alternatively be separated into different wavelength ranges and simultaneously imaged on multiple imaging devices as would be apparent to one skilled in the art.

Similarly to the system 300, to improve operation of the system 600 and to decrease spherical aberration and astigmatism induced by the dispersion unit 650, it may be of interest to lower the numerical aperture of the illumination beam exiting the fiber tip 326. This may be achieved by placing optional light divergence control optics 332 at a predetermined distance from the fiber tip 326.

Similarly to the dispersion unit 350, the dispersion unit 650 may be designed to distribute the focal spots of at least two light beams of at least two different wavelengths originating from the fiber tip 326 to at least two different radial locations on the back focal plane 306 of the high numerical aperture objective 304, thereby providing desired angles of incidence of the light onto a substrate/sample interface 316 and desired depths of the evanescent waves of illumination light of the at least two different wavelengths. The dispersion unit 650 provides controlled chromatic dispersion of the illuminating light of at least two different wavelengths and splitting the at least two-wavelength light into at least two monochromatic beams required, for example, to achieve the same illumination depths for the different wavelengths used. The at least two-wavelength light may be present simultaneously or one at a time or in any combination of wavelengths simultaneously. The dispersion unit 650 may also comprise a beam shifting means (not shown) providing a desired simultaneous absolute offset of a whole set of the at least two individual focal points of different wavelengths without varying the radial distances between them.

The dispersion unit 650 may be configured to provide controlled chromatic dispersion of illuminating light of at least two different wavelengths. The dispersion unit 650 may be implemented in the form of two optical flats 654 and 656 oriented in a V formation with an angle $\theta$ 658 between them. The flats 654 and 656 may be mounted on a rotatable plate 660 such that they rotate together as a unit.

FIGS. 7-1, 7-2 and 7-3 illustrate the example dispersion unit 650 in different orientations.

The direction of rotation of the rotatable plate 660 is denoted by an arrow 755.

The first optical flat 654 is a highly dispersive optical element. In one example, the optical flat 654 may be made of optical glass SF10 or of optical glass SF11. The dispersion of the first optical flat 654 leads to a distance between chief rays $s_{654}(n,\alpha)$ of at least two beams with different wavelengths $\lambda_1$, $\lambda_2$, expressed by equation 10 as:

$$s_{654}(t,n,\alpha) = t_{654} \sin \alpha (\cos \alpha \cdot \Delta n_{654}/(n_{654}^2 - \sin^2 \alpha)^{3/2}) \quad (10)$$

where $t_{654}$ is a thickness the optical flat 654, $\alpha$ 662 is an angle of the normal of the optical flat 654 with respect to the optical axis 330, and $n_{654}$ is an average index of refraction which may be found using equation 11:

$$n_{654} = [n_{654}(\lambda_1) + n_{654}(\lambda_2)]/2 = N_{654} - \Delta n_{654}/2 \quad (11)$$

where $\Delta n_{654} = n_{654}(\lambda_1) - n_{654}(\lambda_2)$, and where $N_{654} = n_{654}(\lambda_1)$.

In general, $N_K = n_K(\lambda_1)$ may be used herein to represent the refractive index of the optical flat K at the reference wavelength $\lambda_1$, where $\lambda_1 < \lambda_2$.

The absolute offset $y_{654}$ provided by the first optical flat 654 is expressed by equation 12 for the reference wavelength $\lambda_1$ as:

$$y_{654}(t_{654}, n_{654}, \alpha) = t_{654} \sin \alpha (1 - \cos \alpha/\text{sqrt}(n_{654}^2 - \sin^2 \alpha)) \quad (12)$$

The second optical flat 656 may be made of low dispersion glass and may be designed to be of a thickness $t_{656}$. In one example, the second optical flat may be made of optical glass BK7. The second optical flat 656 may be mounted at an angle $\theta$ 658 relative to the first optical flat 654, where $0 < \theta < 90°$. Adjusting the angle $\theta$ 658 between the pair of optical flats 654 and 656 may provide lateral displacement of the beam and therefore radial displacement of the focused spots in the back focal plane 306. This displacement may be substantially less than it would be in the case of a single optical flat. The desired thickness $t_{656}$ is expressed by equation 13 as:

$$t_{656} = t_{654}((N_{654}(N_{656} - 1))/(N_{656}(N_{654} - 1))) \quad (13)$$

The low-dispersion second flat 656 provides a smaller dispersion than the first flat 654 and a similar absolute offset, but in the opposite direction from the first flat 654. The distance between chief rays $s_{656}$ and the absolute offset $y_{656}$ provided by the second flat 656 may be found using equations 10 and 12, and by replacing the thickness $t_{654}$ of the optical flat 654 and the angle $\alpha$ 662 with the thickness $t_{656}$ and the angle ($\alpha - \theta$) 664, respectively. This is expressed in equations 14 and 15 as follows:

$$s_{656}(t,n,\alpha-\theta) = t_{656} \sin(\alpha-\theta)(\cos(\alpha-\theta) \cdot \Delta n_{656}/(n_{656}^2 - \sin^2(\alpha-\theta))^{3/2}) \quad (14)$$

$$y_{656}(t,n,\alpha-\theta) = t_{656} \sin(\alpha-\theta)(1 - \cos(\alpha-\theta)/\text{sqrt}(n_{656}^2 - \sin^2(\alpha-\theta))) \quad (15)$$

A total distance between chief rays $S_T(\lambda_1, \lambda_2, \alpha)$ and a total absolute offset $Y_T(\lambda_1, \lambda_2, \alpha)$ provided by the dispersion unit 650 are expressed by equations 16 and 17 below, and may be found using the equations 10, 12, 14 and 15:

$$S_T(\lambda_1, \lambda_2, \alpha) = s_{654}(t_{654}, n_{654}, \alpha) + s_{656}(t_{654}, n_{654}, \alpha-\theta) \quad (16)$$

$$Y_T(\lambda_1, \lambda_2, \alpha) = y_{654}(t_{656}, n_{656}, \alpha) + y_{656}(t_{656}, n_{656}, \alpha-\theta) \quad (17)$$

Figures 1, 7:
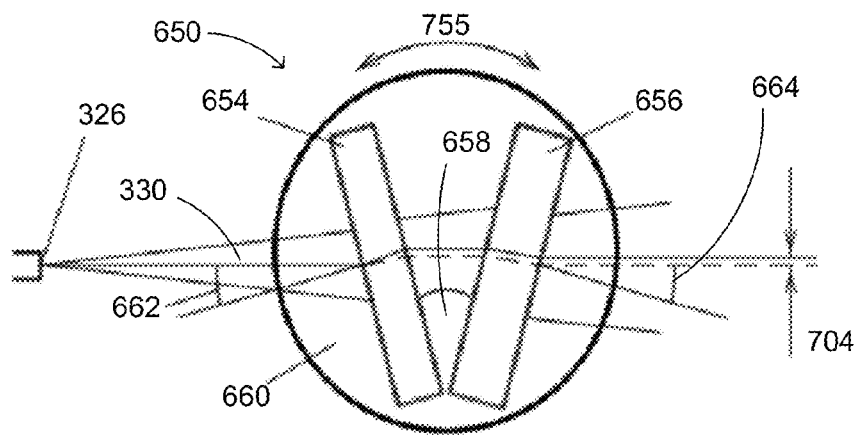
Figures 2, 7:
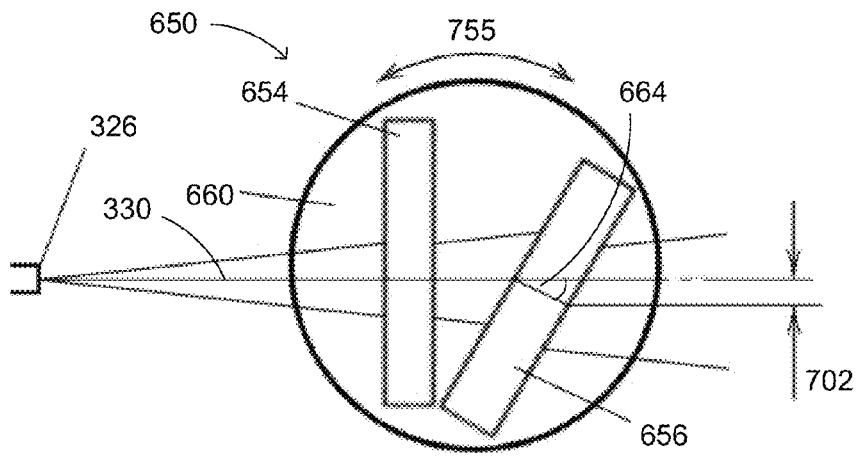
Figures 3, 7:
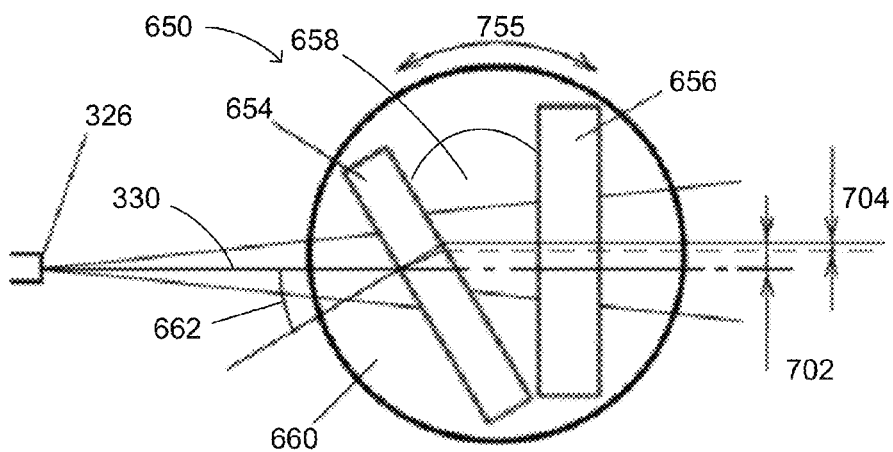

The total absolute offset $Y_T$ is zero when the dispersion unit 650 is in its central position as illustrated in FIG. 7-1. In this position, the angle α 662 is half of the angle θ 658, that is α=θ/2. The total absolute offset $Y_T$ is at its maximum value, denoted by the distance 702, when the dispersion unit 650 is in either one of its limiting positions, that is, when the angle α 662 is zero, as illustrated in FIG. 7-2, or when the angle α 662 is equal to the angle θ 658, as illustrated in FIG. 7-3. The total distance between chief rays $S_T$ is denoted by 704 in FIGS. 7-1 and 7-3.

The total range of the offsets of the proposed dispersion unit 650 of FIGS. 6, 7-1, 7-2 and 7-3 is two times less than the total offset range of the single-plate dispersion unit 350 providing the same lateral dispersion or separation of chief rays of the at least two beams of different wavelengths.

Adjustment of the absolute offset and compensation of the undesired absolute offset may be achieved by simultaneous radial shift of the at least two individual focal points of different wavelengths provided by means of lateral movement of the distal tip 326 of the single mode fiber 324.

Alternatively, compensation of the absolute lateral offset may be achieved by means of lateral movement of the collimating lens 334.

In another example, compensation of the absolute lateral offset may be achieved by means of lateral movement of the imaging lens 336.

In another example, compensation of the absolute lateral offset may be achieved by means of movement of the dichroic mirror 338 along an optical axis 364 of the microscope module 302 or along the optical axis 330 or along both.

In another example, compensation of the absolute lateral offset may be achieved by using any other suitable beam shifting means providing a desired simultaneous lateral shift of the at least two individual focal points, as would be apparent to someone skilled in the art. The beam shifting means may be part of the dispersion unit 650.

In yet another example, compensation of the absolute lateral offset may be achieved by means of steering an optional folding and steering mirror (not shown) or any other beam steering means placed between the collimating lens 334 and the imaging lens 336, as would be apparent to someone skilled in the art.

In practice, a single lens or more than the two lenses 334 and 336 and additional mirrors may be used to direct and control the path of light output from the tip 326 of the fiber 324 and to input the light to the objective 304.

Figure 8:
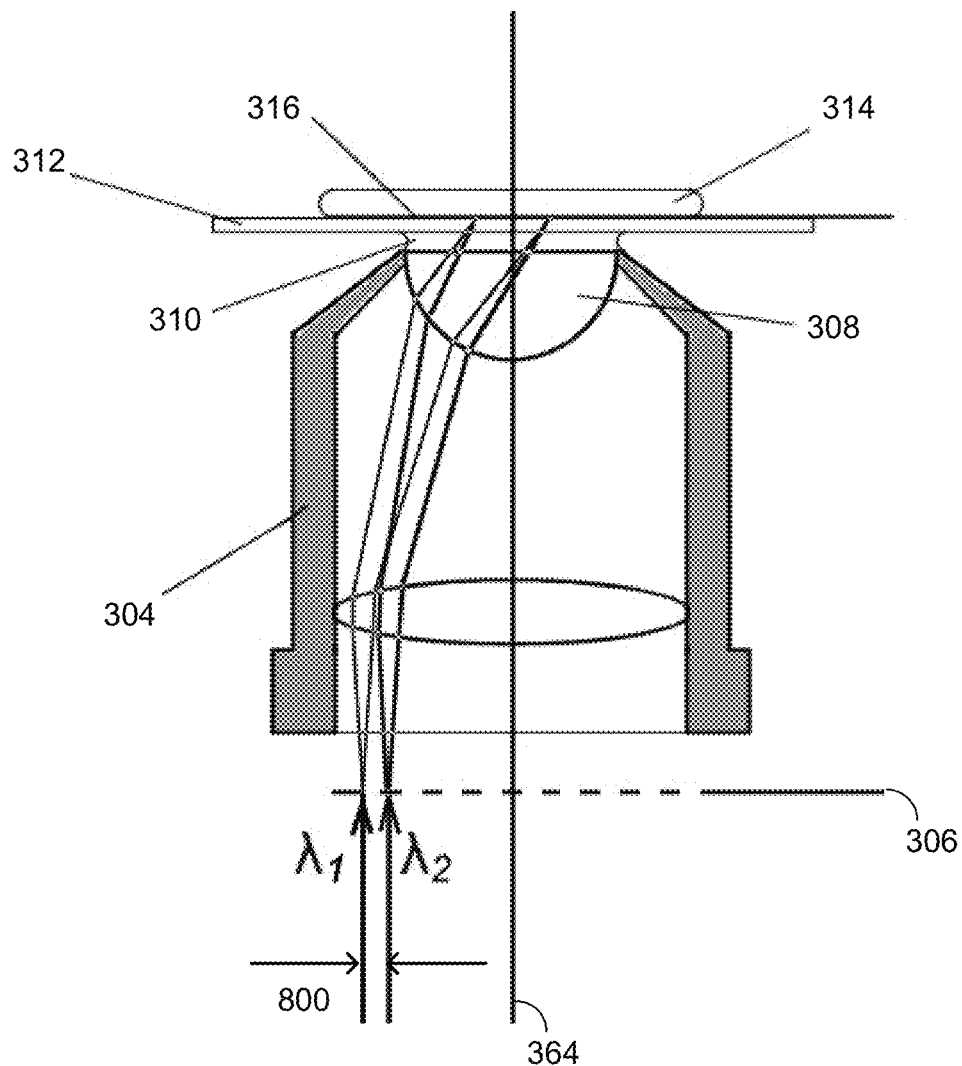
FIG. 8 illustrates a magnified view of the objective lens with the sample in the objective-based TIRF microscopy system of FIG. 6.

FIG. 8 illustrates a magnified view of the objective 304 with the sample 314 in the objective-based TIRF microscope system 600 of FIG. 6.

As described previously, the system 600 provides illumination of the sample 314, which is disposed on the substrate 312. The objective 304 is an oil immersion objective with immersion oil 310 disposed between the substrate 312 and the hemispherical lens 308 of the objective 304.

Due to the addition of the second optical flat 656, the monochromatic beams of illumination light of the different wavelengths $\lambda_1$ and $\lambda_2$ may have focal points that are closer to the back focal plane 306 than achievable with the single optical flat 354 of the dispersion unit 350. For example, the focal points in FIG. 8 are located substantially at the back focal plane 306, whereas the focal points in FIG. 5 are shifted from the back focal plane 306 by the distances 502 and 504, respectively.

IN OPERATION: Returning to the system illustrated in FIG. 6, illumination light of at least two different wavelengths, $\lambda_1$ and $\lambda_2$, is delivered from the light source 322 through the single mode optical fiber 324. The light diverges or spreads out from the distal end 326 of the fiber 324, and passes through the optional divergence control lens 332 and through the optical flats 654 and 656 of the dispersion unit 650.

The illumination light is split by the optical flats 654 and 656 into at least two monochromatic beams of different wavelengths, $\lambda_1$ and $\lambda_2$, with a total dispersion $S_T$ given by equation 16, and a total radial offset $Y_T$ given by equation 17. The total absolute lateral offset of the at least two beams of different wavelengths may be compensated, for example, by means of lateral movement of the distal tip 326 of the fiber 324, where the lateral direction is denoted by arrow 224. After passing through the dispersion unit 650, the chief rays parallel to the optical axis 330 pass through the collimating lens 334. The light is collimated by the collimating lens 334, which provides at least two collateral partially overlapping collimated beams travelling toward the imaging lens 336. The light is refocused by the imaging lens 336 before being reflected by the dichroic mirror 338 along the optical axis 364 and toward the outer edge of the microscope objective 304.

The imaging lens 336 focuses the illumination beams substantially onto the back focal plane 306 of the objective 304, so that the lenses 334 and 336 provide an image of the fiber tip 326 onto the back focal plane 306.

The relative distance ΔR between the two focal points of the different wavelengths, $\lambda_1$ and $\lambda_2$, is illustrated at 800 in FIG. 8 and is expressed by equation 18 as:

$$\Delta R = Y_T F_{336}/F_{334} \qquad (18)$$

The objective 304 directs the monochromatic beams of illumination light travelling along the outer edge of the objective lenses of the objective 304 so that light exiting the hemispherical lens 308 and passed through the immersion oil 310 and the substrate 312 strikes the interface 316 between the sample 314 and the substrate 312 with angles of incidence that are greater than the critical angle and provide the desired depths of the evanescent waves of illumination light of the at least two different wavelengths.

Rotation of the dispersion unit 650 and lateral shifting of the fiber tip 326 may allow the user to adjust the radial locations of the focal spots of at least two converging monochromatic light beams of the two different wavelengths, $\lambda_1$ and $\lambda_2$, on the back focal plane 306. As a result, it is possible to tune the relative penetration depths of evanescent illumination light of different wavelengths, for example, to obtain depths that are as similar as possible for different wavelengths.

Fluorescent light emitted from the sample 314 near the interface 316 may be captured by the hemispherical lens 308 of the microscope objective 304 at the operating numerical aperture NA of the microscope objective 304. The collected fluorescent light further passes through the dichroic mirror 338 and the blocking filter 348, and is focused by the lens 349 onto the image plane 346, which coincides with a detection plane of the image sensor 344 of the imaging device 342.

Although not explicitly illustrated, it will be apparent to someone skilled in the art that the example dispersion unit 350 or 650 may alternatively be mounted between the imaging lens 336 and the pick-off mirror or the dichroic mirror 338.

What is claimed is:

1. A method for a multiple wavelength total internal reflection fluorescence (TIRF) microscopy system comprising an objective, the method comprising:

receiving, at a dispersion unit of the microscopy system, illumination light having at least a first wavelength $\lambda_1$ and a second wavelength $\lambda_2$, where $\lambda_1 \ne \lambda_2$;

splitting, at the dispersion unit comprising a high-dispersion optical element, the illumination light into a first monochromatic beam having the first wavelength $\lambda_1$ and a second monochromatic beam having the second wavelength $\lambda_2$;

focusing the first monochromatic beam and the second monochromatic beam onto a back focal plane of the objective, near an outer edge of the objective, such that the first monochromatic beam is focused onto the back focal plane at a first focal point located at a first radial distance $R_1$ from an optical axis of the objective and the second monochromatic beam is focused onto the back focal plane at a second focal point located at a second radial distance $R_2$ from the optical axis of the objective, where $R_1 \ne R_2$; and while maintaining a radial separation between the first focal point and the second focal point at the back focal plane, rotating the dispersion unit in order to adjust angles of incidence of the monochromatic beams onto an interface between a substrate and a sample to be imaged, thereby adjusting depths of evanescent waves within the sample, wherein the angles of incidence differ from each other and are greater than the critical angle and wherein the evanescent waves are generated by the monochromatic beams.

2. The method as claimed in claim 1, wherein the high-dispersion optical element comprises optical glass SF10 or optical glass SF11.

3. The method as claimed in claim 1, wherein the dispersion unit comprises an optical flat that is the high-dispersion element mounted on a rotatable plate and wherein rotating the dispersion unit comprises rotating the rotatable plate.

4. The method as claimed in claim 1, wherein the dispersion unit comprises a first optical flat and a second optical flat mounted on a rotatable plate such that there is a non-zero angle between a normal of the first optical flat and a normal of the second optical flat, wherein the first optical flat is the high-dispersion optical element and the second optical flat is a low-dispersion optical element, and wherein the illumination light passes through the first optical flat before passing through the second optical flat.

5. The method as claimed in claim 4, wherein the low-dispersion optical element comprises optical glass BK7.

6. The method as claimed in claim 4, wherein the angle is less than 30 degrees.

7. The method as claimed in claim 1, wherein the dispersion unit comprises a first optical flat and a second optical flat mounted on a rotatable plate such that there is a non-zero angle between a normal of the first optical flat and a normal of the second optical flat, wherein the first optical flat is a low-dispersion optical element and the second optical flat is the high-dispersion optical element, and wherein the illumination light passes through the first optical flat before passing through the second optical flat.

8. The method as claimed in claim 7, wherein the low-dispersion optical element comprises optical glass BK7.

9. The method as claimed in claim 7, wherein the angle is less than 30 degrees.

10. The method as claimed in claim 1, wherein the illumination light has exited a distal end of a single mode optical fiber prior to being received at the dispersion unit.

11. The method as claimed in claim 10, further comprising:

passing the illumination light exiting the distal end of the optical fiber through light divergence control optics prior to receiving the illumination light at the dispersion unit.

12. The method as claimed in claim 10, further comprising:

passing the illumination light exiting the distal end of the optical fiber through a collimating lens and through an imaging lens prior to receiving the illumination light at the dispersion unit.

13. The method as claimed in claim 1, further comprising:

passing the monochromatic beams exiting the dispersion unit through a collimating lens and through an imaging lens.

14. A multiple wavelength total internal reflection fluorescence (TIRF) microscopy system, comprising:

an objective;

a dispersion unit comprising a high-dispersion optical element, the dispersion unit positioned to receive illumination light having at least a first wavelength $\lambda_1$ and a second wavelength $\lambda_2$, where $\lambda_1 \ne \lambda_2$, and to split the illumination light into a first monochromatic beam having the first wavelength $\lambda_1$ and a second monochromatic beam having the second wavelength $\lambda_2$; and optical elements to focus the first monochromatic beam and the second monochromatic beam onto a back focal plane of the objective, near an outer edge of the objective, such that the first monochromatic beam is focused onto the back focal plane at a first focal point located at a first radial distance $R_1$ from an optical axis of the objective and the second monochromatic beam is focused onto the back focal plane at a second focal point located at a second radial distance $R_2$ from the optical axis of the objective, where $R_1 \ne R_2$, wherein the dispersion unit is rotatable in order to adjust angles of incidence of the monochromatic beams onto an interface between a substrate and a sample to be imaged, thereby adjusting depths of evanescent waves within the sample, wherein, while rotating the dispersion unit, a radial separation is maintained between the first focal point and the second focal point on the back focal plane, wherein the angles of incidence differ from each other and are greater than the critical angle and wherein the evanescent waves are generated by the monochromatic beams.

15. The system as claimed in claim 14, wherein the high-dispersion optical element comprises optical glass SF10 or optical glass SF11.

16. The system as claimed in claim 14, wherein the dispersion unit comprises an optical flat that is the high-dispersion element mounted on a rotatable plate.

17. The system as claimed in claim 14, wherein the dispersion unit comprises a first optical flat and a second optical flat mounted on a rotatable plate such that there is a non-zero angle between a normal of the first optical flat and a normal of the second optical flat, wherein the first optical flat is the high-dispersion optical element and the second optical flat is a low-dispersion optical element, and wherein the illumination light passes through the first optical flat before passing through the second optical flat.

18. The system as claimed in claim 17, wherein the angle is less than 30 degrees.

19. The system as claimed in claim 14, wherein the dispersion unit comprises a first optical flat and a second optical flat mounted on a rotatable plate such that there is a non-zero angle between a normal of the first optical flat and a normal of the second optical flat is a low-dispersion optical element and the second optical flat is the high-dispersion optical element, and wherein the illumination light passes through the first optical flat before passing through the second optical flat.

20. The system as claimed in claim 19, wherein the angle is less than 30 degrees.

\* \* \* \* \*